United States Patent [19]

Chisholm et al.

[11] Patent Number: 5,057,622

[45] Date of Patent: Oct. 15, 1991

[54] S-ALKYLTHIOPROPIONIC ACIDS AND DERIVATIVES

[75] Inventors: Daniel R. Chisholm, Warwick, N.Y.; Michael H. Fisch, Wayne, N.J.; Mark E. Flanagan, Ft. Collins, Colo.; Richard D. Peveler, Woodcliff Lake, N.J.

[73] Assignee: Witco Corporation, New York, N.Y.

[21] Appl. No.: 627,542

[22] Filed: Dec. 10, 1990

Related U.S. Application Data

[63] Continuation of Ser. No. 394,547, Aug. 16, 1989, abandoned.

[51] Int. Cl.$^5$ .................. C07C 319/14; C07C 323/52
[52] U.S. Cl. ..................................... 560/152; 562/512
[58] Field of Search ................ 560/152, 154; 562/512

[56] References Cited

U.S. PATENT DOCUMENTS

| | | | |
|---|---|---|---|
| 2,416,052 | 2/1947 | Gribbins | 260/398.5 |
| 2,601,063 | 6/1952 | Smith et al. | 260/481 |
| 2,680,107 | 6/1954 | Leistner et al. | 260/45.75 |
| 3,144,422 | 8/1964 | Homberg | 260/23 |
| 3,249,632 | 5/1966 | Peterson et al. | 524/291 |
| 3,517,058 | 6/1970 | Thoma et al. | 260/526 |
| 3,629,194 | 12/1971 | Onishi et al. | 260/45.85 |
| 3,637,809 | 1/1972 | Kleiner | 524/289 |
| 3,758,549 | 9/1973 | Dexter et al. | 260/481 R |
| 4,080,364 | 3/1978 | Kauder et al. | 260/45.85 H |
| 4,101,550 | 7/1978 | Spivack | 529/291 |
| 4,125,516 | 11/1978 | Dexter et al. | 260/45.8 N |
| 4,226,991 | 10/1980 | Nakahara et al. | 544/221 |
| 4,349,468 | 9/1982 | Nakahara et al. | 524/302 |
| 4,774,355 | 9/1988 | Omori et al. | 560/152 |
| 4,794,138 | 12/1988 | Dunski et al. | 524/289 |

OTHER PUBLICATIONS

"Reactions of Mercaptans with Acrylic and Methacrylic Derivatives", Hurd et al., *Journal of American Chemical Society,* vol. 60, pp. 2328-2335, Oct. 1947.
"Methyl 3-n-Dodecylmercaptopropionate", *Journal of American Chemical Society,* vol. 73, p. 4050, 1951.
Smith et al., "Addition of Thioglycolic Acid to Alpha-Alkenes", ACTA Chemica Scandinavica, vol. 8, No. 7, 1954.

*Primary Examiner*—Veronica P. Hoke
*Attorney, Agent, or Firm*—Lockwood, Alex, Fitzgibbon & Cummings

[57] ABSTRACT 3-alkylthiopropionic acids are provided which are a direct addition reaction product of an alkylmercaptan and acrylic acid of an alkali metal salt thereof, the reaction being carried out by heating the reactants in the presence of an aqueous alkaline solution having a pH of at least about 11. The acids can be esterified with pentaerythritol in order to form tetraesters which are especially useful as stabilizers for polymer resins and polymers.

13 Claims, No Drawings

S-ALKYLTHIOPROPIONIC ACIDS AND DERIVATIVES

This application is a continuation of application Ser. No. 394,547, filed Aug. 16, 1989, now abandoned.

BACKGROUND AND SUMMARY OF THE INVENTION

The present invention generally relates to a process for preparing S-alkylthiopropionic acids, as well as derivatives thereof and the products thus produced. More particularly, the invention relates to the preparation of 3-alkylthiopropionic acids and derivatives by directly reacting a mercaptan with acrylic acid or acrylate salt, the direct reaction being an addition reaction carried out in the presence of a strong base catalyst. When the 3-alkylthiopropionic acid is esterified with pentaerythritol or the like, the product formed has an extremely high level of ester having the tetraester structure.

Alkyl esters derived from alkylthioalkanoic acids and the like are, in general, known to be useful as stabilizers of organic materials such as polymer resins and the like which are otherwise subject to thermal and oxidative deterioration during processing, extrusion or molding, as well as during use. Esters having this general utility have in the past been prepared by various procedures. Dexter et al U.S. Pat. No. 3,758,549, for example, basically teaches transesterification procedures for the preparation of these types of products. By such procedures, it is often difficult to obtain a product that has a tetraester content at or above 90% by weight, particularly when the transesterification is carried out on an industrial scale.

Stabilizers for enhancing the resistance of polyolefins to deterioration can also be prepared by reacting an alpha-olefin with a multi-functional ester of a mercaptocarboxylic acid. Stabilizers of this type and the process for their preparation are disclosed in Kauder et al U.S. Pat. No. 4,080,364. Experience with this type of addition reaction indicates the product thus formed has a tetraester content which typically does not meet or exceed 90% by weight.

Nakahara et al U.S. Pat. No. 4,349,468 teaches the preparation of a pentaerythritol tetrakis (3-laurylthiopropionate) stabilizer for polyolefins which is produced by a process including heating an alpha-olefin such as 1-dodecene with a beta-mercaptopropionic acid or ester in the presence of an azonitrile or peroxide catalyst, followed by esterifying the resultant alkylthiopropionic acid with pentaerythritol. The resulting product is typically inferior in that the alpha-olefin reaction produces an unwanted isomer byproduct that, if not removed in a separate purification step, lowers the quality of the pentaerythritol ester.

Alkylthiopropionic acids prepared by approaches such as these do not typically directly produce, without special purification, an alkylthiopropionic acid which exhibits a high purity characteristic which will, when reacted with pentaerythritol or the like, form an ester product which has an extremely high tetraester content and a minimum of other components such as the triester. Furthermore, this advantageous result is typically achieved by the present invention without requiring a substantially high excess of the acid reagent, thereby minimizing the cost and inefficiency of having to remove excess acid from the reaction product and without purification at an intermediate stage.

By the present invention, a 3-alkylthiopropionic acid having about 4 to about 20 carbon atoms in the alkyl group is prepared by directly reacting an alkyl mercaptan having between about 4 and about 20 carbon atoms with an alkali metal acrylate, the reaction being carried out in the presence of a strong base catalyst, typically within an aqueous alkaline solution having a pH of at least about 11. Thereafter, the reaction solution is acidified to a pH which is at about 4 or below, and the 3-alkylthiopropionic acid is then recovered from the water-insoluble phase of the acidified reaction solution. When desired, a high purity tetraester product is formed by esterification of the 3-alkylthiopropionic acid with pentaerythritol or the like.

It is accordingly a general object of the present invention to provide an improved process for preparing an alkylthiopropionic acid and to provide an improved acid prepared by the process.

Another object of the present invention is to provide an improved process for preparing an S-alkylthiopropionic acid by a direct addition reaction process which results in the recovery of an S-alkylthiopropionic acid which is of exceptional purity.

Another object of this invention is to provide an improved method for providing a 3-alkylthiopropionic acid which is especially suitable for use in preparing a 3-alkylthiopropionate tetraester.

Another object of the present invention is to provide an improved process for the work-up purification of a tetraester formed from the 3-alkylthiopropionic acid.

These and other objects, features and advantages of the present invention will be clearly understood through a consideration of the following detailed description.

DESCRIPTION OF THE PARTICULAR EMBODIMENTS

The 3-alkylthiopropionic acids prepared according to the present invention are made by a direct addition reaction procedure which is carried out in order to minimize the recovery of anything other than the desired 3-alkylthiopropionic acid. The length of the carbon chain of the alkyl group within the 3-alkylthiopropionic acid is selected by the carbon chain length of the mercaptan which is charged into the reaction vessel. The selected mercaptan undergoes an addition reaction with an acid reactant or salt thereof to add the propionic acid component of the 3-alkylthiopropionic acid.

With more particular reference to the mercaptan, same has the formula RSH, wherein R has a carbon chain length of between about 4 and about 20 carbon atoms. Exemplary reactants in this regard include n-butylmercaptan, n-octylmercaptan, n-decylmercaptan, n-dodecylmercaptan and the like. Generally equimolar charges of this mercaptan and the other addition reactant are incorporated into the reaction vessel, although the acid component may be present at a concentration slightly in excess of the equimolar level.

Concerning the other addition reactant, which may be characterized as the acid reactant, same can be charged to the reaction vessel as acrylic acid or as a derivative, typically an alkali metal salt thereof. Because the addition reaction is run under strongly basic conditions, the acid reactant is perhaps more properly characterized as an alkali metal acrylate, with the alkali metal being that of the base component which catalyzes the addition reaction.

Any strong base can be utilized as the catalyst, provided an aqueous solution thereof will impart a pH of at least about 11 to the reaction composition. The strength of the base can be generally defined as one wherein a 1% aqueous solution thereof has a pH of at least about 13. Typical strong bases in this regard include aqueous potassium hydroxide, aqueous sodium hydroxide and the like. It is important that the reaction composition incorporate an adequate concentration of this strong base. The amount is to be adequate to convert any charged acrylic acid to its alkali salt, while still providing enough strong base to act as a catalyst for the addition reaction. For example, the reaction composition should typically include at least about 1.05 mole of strong base per mole of acrylic acid charged into the reaction vessel.

The base catalyzed addition reaction is carried out with a sufficient quantity of solvent within the reaction composition. Preferably, the solvent is a mixture of organic solvent and water. Water alone may be suitable for acids made from mercaptans with short chain lengths such as C4, but using the solvent mixture is believed to be important in most cases. For example, the reaction is faster and less subject to foaming when the solvent is water combined with an organic solvent. Preferred organic solvents in this regard are oxygenated organic solvents, typically ones that are water-soluble oxygenated compounds exhibiting a ratio of from one to four carbon atoms for every oxygen atom. Exemplary solvents in this regard include 2-propanol, tert-butyl alcohol, tetrahydrofuran, ethanol, methanol, 2-ethoxyethanol, and the like. An especially preferred solvent is a mixture of water and 2-propanol (isopropyl alcohol). A typical ratio of water to oxygenated organic solvent is between about 9 to 1 and about 1 to 9.

In a preferred aspect of the present process, the mercaptan is added to the reactant composition after it already contains the alkali metal acrylate. It has been determined that, even when the reaction is carried out in the presence of oxygen, the incidence of undesirable disulfide formation is reduced significantly with this order of addition of reactants, when compared with the reverse order of addition, which can be characterized as the addition of acrylic acid to the reaction composition which already contains sodium mercaptide. When the reverse order of addition is desired, typically adequate control of disulfide formation can be attained by blanketing the reaction mixture with nitrogen, when this is feasible.

After the addition reaction has progressed to the desired extent, the alkylthiopropionic acid is isolated from the reaction composition by proceeding first with acidification of the reaction mixture, typically with a suitable aqueous mineral acid. Aqueous and organic layers thereby defined are then separated. If necessary, depending upon the carbon chain length of the mercaptan reactant, the layers are maintained at a temperature high enough to keep the alkylthiopropionic acid molten. After separation has been completed, the collected organic phase is preferably vacuum stripped in order to remove and recover the organic solvent and thereby provide the 3-alkylthiopropionic acid addition reaction product.

When it is desired to esterify the 3-alkylthiopropionic acid, such as into its tetraester with pentaerythritol, this is typically carried out at an elevated temperature and under acid catalysis. Typically suitable catalysts in this regard are para-toluenesulfonic acid, xylenesulfonic acid, methanesulfonic acid, ethanesulfonic acid and the like.

It is especially preferred that this esterification procedure be followed by an operation wherein the organic phase is solvent refined with an organic solvent. Preferably, the solvent refining medium is a blend of at least two organic solvents which is particularly well suited for the specific alkylthiopropionic tetraester being prepared. One component of the solvent mixture is preferably 2-propanol. Other exemplary components of this type of solvent blend include other low molecular weight alcohols and low molecular weight esters, including materials such as methanol, ethanol, isopropyl alcohol, ethyl acetate, isopropyl acetate, and the like. It has been found that a suitable solvent blend will improve work-up purification procedures, when desired, in a manner that minimizes the expense thereof. These solvent blends minimize the need to solve the dilemma created by the fact that an especially high excess of the alkylthiopropionic acid will favor the formation of the tetraester over the less desirable triester, but such excess acid must be removed as an undesirable impurity from the tetraester.

As an example of suitable organic solvent blends, a blend of isopropanol and isopropyl acetate has been found to be an especially suitable refining solvent for recovering the crystalline tetraester of 3-dodecylmercaptopropionic acid with pentaerythritol. A blend of methanol and isopropanol is generally preferred for the work-up purification of the liquid tetraester of 3-octylmercaptopropionic acid with pentaerythritol. It has been found that this solvent blend is non-miscible with this tetraester and performs well as an extracting solvent for any triester impurity and unreacted octylmercaptopropionic acid. A typical two-component solvent blend would be at a ratio of between about 9 to 1 and about 1 to 9.

Esters of the type discussed herein are typically suitable for use as stabilizers for polymers. The tetraesters with pentaerythritol have been found to be especially useful as stabilizers for a class of proprietary polymers and polymer blends having a terephthalate ester component and a rubbery type of component. Articles extruded from these types of proprietary polymers have superior impact resistance properties and can be suitable for use as automobile bumpers and the like. The 3-dodecylthiopropionate tetraester of pentaerythritol has been observed to be generally equal in performance to similar ester stabilizers manufactured on a commercial scale by a process believed to be more complicated than the straightforward addition reaction and subsequent esterification procedure of the present invention.

Various tetraester stabilizers prepared according to this invention have different physical properties which may be particularly advantageous for different proprietary polymers. For example, esters made from dodecylmercaptan are solid at room temperature and less likely to exhibit a noticeable odor when in use as a stabilizer. Esters made from octylmercaptan are basically liquid at room temperature, are less waxy than esters having a greater molecular weight, and can be more compatible, particularly with polymer resins that tend to be liquid at room temperature. Esters prepared from decylmercaptan typically have properties thereinbetween, and they can exhibit good compatibility without excessive volatility.

The following examples illustrate the present invention, as well as procedures previously used or taught for preparing acids and/or stabilizer esters having chemical structures generally along the lines of those prepared according to the present invention.

EXAMPLE 1

To a stirred solution of 101.2 grams (0.50 mole) of 1-dodecylmercaptan in 100 ml. of isopropanol under a nitrogen atmosphere at 25° C., 46.2 grams (0.58 mole) of 50% sodium hydroxide aqueous solution was added in one portion. The mixture exothermed to 70° C., and a white precipitate formed. Isopropyl alcohol (50 ml.) was added to the slurry, which was cooled to 32° C. with a water bath. 37.8 grams (0.525 mole and 36 ml.) of acrylic acid was added dropwise over a 15 minute period. Additional isopropyl alcohol (50 ml. in two aliquots) was added, the exothermal reaction proceeded at 40° C., and after 20 minutes of stirring, an additional 50 ml. of water was added. The solid components slowly dissolved in order to provide a homogeneous solution, which was refluxed for two hours. After standing overnight at 25° C., the sample was analyzed to have 0.03% dodecylmercaptan.

Acidification was carried out by heating the reaction composition to 45° C. and adding 58.3 grams of 50% aqueous sulfuric acid, after which same was poured into a separatory funnel, and the aqueous layer was drained. Washing was next carried out with three 100 ml. portions of water, with the third wash including a small amount of sodium sulfate. The washed organic layer was then vacuum stripped with a Roto-Vap rotary evaporator to give 128.6 grams of 3-dodecylthiopropionic acid product having a melting point of 59°–62° C. The yield by GLC was 99.0% having an acid value of 204.2 (theory 204.4).

EXAMPLE 2

The procedure of Example 1 was substantially followed, except the 1-dodecylmercaptan or 1-dodecanethiol was added dropwise over a 50-minute time span to the sodium acrylate solution, and the reaction then was continued as follows. The reaction mixture exhibited two phases, and no temperature change was noted. The reaction mixture was heated to reflux, and the resulting clear solution was refluxed for two hours and allowed to stand overnight at 25° C. under nitrogen gas. It was then warmed to 50° C. to give a clear solution, and 58.3 grams of of 50% aqueous sulfuric acid was added. After pouring the composition into a separatory funnel, the aqueous layer was drained, and the organic layer was washed with three 100 milliliter aliquots of hot water containing a small amount of sodium sulfate. After vacuum stripping, 130.3 grams of 3-dodecylthiopropionic acid product was collected, having a laurylmercaptan percentage of 0.02%, an acid value of 202.9 (204.4 theoretical), and a derivatized GLC of 97.6% (derivatization being necessary because of an inadvertent cut-off of a portion of peak).

EXAMPLE 3

The same basic ingredients and quantities thereof were reacted as specified in Example 1, except the initial reaction composition included 75 ml. of isopropanol and 50 ml. of water. The resulting clear solution was cooled to 60° C., and the 1-dodecylmercaptan or laurylmercaptan was added during a 30-minute time period. No temperature change was noted, the composition was heated to reflux, and 25 ml. of water were added. Adding 25 ml. of isopropyl alcohol resulted in a clear solution, which was refluxed for 3 hours, moderate foaming being observed. After cooling, 58.3 grams of 50% aqueous sulfuric acid were added, and the composition was poured into a separatory funnel and washed with three 100 mililiter aliquots of hot water with sodium sulfate. Vacuum stripping yielded 134.5 grams of 3-dodecylthiopropionic acid product having a melting point of 60°–62.5° C., an acid value of 202.5 (204.4 theoretical), a laurylmercaptan percentage of 0.02%, and a yield of 98.2% by GLC.

EXAMPLE 4

To a stirred solution of 75.6 grams (1.05 mole, 72 ml.) of acrylic acid in 200 ml. of isopropanol under nitrogen gas at 25° C. a solution of 46.2 grams (1.16 mole) of sodium hydroxide in 246 ml. of water was added. The temperature was then at 55° C., and 202.4 grams (1.00 mole, 239.6 ml.) of 1-dodecanethiol were added dropwise over 40 minutes, the temperature exotherming to 58° C. A clear solution was visible at this point, and the reactant composition was heated to reflux for three hours, cooled to 60° C., and 117 grams of 50% aqueous sulfuric acid were added, followed by stirring for 30 minutes. After separation and vacuum stripping at 100° C. at 25 mmHg for 1 hour, the yield was 270.7 grams of 3-dodecylthiopropionic acid product having a melting point of 58.5°–62° C., a laurylmercaptan content of 0.03%, an acid value of 204.05, and a yield by GLC in excess of 98.0%.

EXAMPLE 5

259.7 grams (0.946 mole) of 3-dodecylthiopropionic acid as prepared in accordance with Example 4, 30.67 grams (0.225 mole) of pentaerythritol, and 4.50 grams (0.024 mole) of hydrated para-toluenesulfonic acid were heated to 135° C. With stirring. After the mixture had become molten, a vacuum of 20 mmHg was carefully applied, and stirring proceeded for 4 hours at 135° C. The reaction composition was then poured into a separatory funnel containing 200 ml. of warm water and 6.647 grams (17.49 mmoles) of trisodium phosphate. An emulsion resulted, which was broken by adding sodium sulfate and placing the separatory funnel in an oven at 80° C. After separation, washing proceeded with 200 ml. of warmed water containing a small amount of sodium sulfate, followed by vacuum stripping. The yield was 255.2 grams having a melting point of 46°–49.5° C. and an acid value of 8.76. Analysis showed 91.6% 3-dodecylthiopropionic tetraester of pentaerythritol and 8.4% of the triester. Several solvents were investigated for the refining of the crude 3-dodecylthiopropionic acid ester of pentaerythritol product.

The crude ester (initial melting point of 45°–49° C.) as heated with each test solvent, with stirring, using 1.5 volume of solvent per weight of crude ester, until a clear solution was obtained. The solution was allowed to cool to 26° C. ambient temperature and crystallize for three hours. The crystals were collected, washed with a portion of the same solvent at 26° C., dried in a vacuum desiccator, and weighed. The percent recovery and the melting point for esters recovered by each of the solvents are specified below, the acetate/alcohol runs illustrating the invention, with the others being provided for comparative purposes.

| Solvent | % Recovery | Melting Point |
| --- | --- | --- |
| isopropyl acetate/ isopropanol 1:1 | 85% | 48–52° C. |
| isopropyl acetate/ isopropanol 1:3 | 75% | 48–51° C. |
| isopropyl acetate/ isopropanol 1:4 | 86% | 48–51° C. |
| isopropyl acetate/ isopropanol 3:7 | 88% | 48–51° C. |
| isopropyl acetate/ isopropanol 1:6 | 85% | 48–51° C. |
| isopropyl acetate/ isopropanol 1:9 | 85% | 48–52° C. |
| ethyl acetate/ isopropanol 1:1 | 67% | 48–51° C. |
| toluene/ isopropanol 1:1 | 0% | — |
| methanol/ THF 1:1 | 76% | 46–49° C. |
| heptane | 58% | 48–51° C. |
| methylethyl ketone | 46% | 48–51° C. |
| dibutyl ether | 78% | 44–47° C. |
| 2-butoxyethanol | 85% | 50–51° C. |
| 2-methoxyethanol | none (oiled out) | — |
| ethanol | none (oiled out) | — |
| acetonitrile | none (oiled out) | — |
| isopropanol | none (oiled out) | — |
| isopropanol acetate | 70% | 48–51° C. |
| ethyl acetate | 0% | — |
| acetone | 77% | 48–51° C. |

The melting point point improvements of some of the runs indicates that impurities (free acid and triester) are removed. The ester/alcohol mixtures according to the invention are safer than, for example acetone, because of higher boiling point and flash point, they gave better results than heptane, alcohols alone, or esters alone, and the respective boiling points of 2-butoxyethanol and of dibutyl ether are higher than desirable for production feasibility.

EXAMPLE 6

A charge of 146.3 grams (1.00 mole) of n-octylmercaptan, 200 m. of isopropyl alcohol and 200 ml. of water were added to a round bottom flask. At room temperature, 46.4 grams (1.16 mole) of sodium hydroxide in 46.4 ml. of water were added to the flask, and exotherm proceeded at 50 to 60° C. Over a 30-minute period, 75.1 grams (1.05 mole) of acrylic acid were added dropwise, and the temperature was then raised to 85° C. and the mixture was allowed to reflux for 2 hours. After cooling to 55° C., 83 grams of 70% aqueous sulfuric acid (0.59 mole) were added, with stirring for 30 minutes, followed by pouring into a separatory funnel. The aqueous layer was drained off and the organic layer was washed with an equal volume of water containing 2% sodium sulfate. After vacuum stripping at 60° C., the reaction product was analyzed to contain 0.04% octylmercaptan and a yield of 98.6% of 3-octylthiopropionic acid product.

EXAMPLE 7

205.6 (0.441 mole) of the 3-octylthiopropionic acid prepared in Example 6, 30.5 grams (0.224 mole) of pentaerythritol, and 2.24 grams (0.013 mole) of para-toluene sulfonic acid catalyst were added to a round bottom flask. A vacuum of approximately 20 mmHg was applied, and the temperature was raised to 135° C. and held there for 5 hours, with stirring, in order to thereby remove water. The composition was allowed to cool to about 50° C., after it was poured into a separatory funnel and washed with 50 ml. of water containing 11.9 grams of trisodium phosphate. After the aqueous layer was drained, the organic layer was washed with two aliquots of 125 ml. of 4% sodium sulfate and once with 200 ml. of a 4 to 1 blend of methanol and isopropyl alcohol. Vacuum stripping and filtering yielded a reaction product having an acid value of 1.05 and analyzing at 0.024% of n-octylmercaptan and a yield of at least 94% 3-octylthiopropionic tetraester of pentaerythritol product. Chromatagram analysis indicated that the finished product contained 94.6% tetraester and 4.2% triester.

EXAMPLE 8

S-octylthiopropionic acid was synthesized by proceeding generally in accordance with Example 6, except the n-octylmercaptan was added to the acrylate salt. The result was a 99% yield of 3-octylthiopropionic acid product, having an acid value of 255.27 (256.9 theory) and an n-octylmercaptan analysis of 0.14%.

EXAMPLE 9

The procedure generally in accordance with Example 7 was followed, using 200.1 grams (0.916 mole) of the 3-octylthiopropionic acid product of Example 8, together with 29.7 grams (0.218 mole) of pentaerythritol, and 2.26 grams (0.013 mole) of para-toluenesulfonic acid. The resulting product, after solvent refining with a 4:1 blend of methanol and isopropanol, analyzed at 0.01% of n-octylmercaptan and had an acid value of 0.04. Chromatogram analysis showed a product tetraester peak at 5.48 minutes, indicating 97.9% of the pentaerythritol tetraester of 3-octylpropionic acid product, and a triester impurity peak at 4.12 minutes, amounting to 1.3% of the product.

EXAMPLE 10

To a stirred slurry of 607.2 grams (3.00 moles) of laurylmercaptan in 1200 ml. of 1:1 water/isopropanol at 25° C. under nitrogen atmosphere was added 276.8 grams (3.46 moles) of a 50% aqueous sodium hydroxide solution. The reaction composition exothermed to 46° C. Then, 226.8 grams (3.15 moles) of acrylic acid were added dropwise over 35 minutes, and the reaction composition exothermed to 68° C. The reaction composition was then refluxed for 3 hours. After cooling slightly, 248.6 grams (1.77 moles) of 70% aqueous sulfuric acid was added, and additional acid was added as needed until the pH reached 3. The composition was then poured into a separatory funnel, and the aqueous layer was drained. The organic layer was washed three times with 800 ml. of hot 3% aqueous sodium sulfate. Residual isopropanol and water were vacuum stripped at 60°–70° C. and 70 mmHg until nothing further distilled. The temperature was raised to 100° C. and the pressure was reduced to 25 mmHg to remove any residual acrylic acid. The yield of 3-dodecylthiopropionic acid product was 813.5 grams, with a melting point of 60°–62° C., an acid value of 203.8 (theory 204.4), and a percent laurylmercaptan of 0.046%. The percent yield was 98.8%.

EXAMPLE 11

Approximately 100 ml. water and 14.4 grams (0.2 mole) of acrylic acid were added to a flask and stirred.

Then, 16 grams (0.2 mole) of a 50% solution of sodium hydroxide were added, followed by 18 grams (0.2 mole) of n-butylmercaptan from a dropping funnel. At the start of the addition, the sodium acrylate solution was at 40° C. as a result of the neutralization exotherm. After adding approximately one-half of the butyl mercaptan, a second liquid phase had formed. Addition was interrupted, and the flask was heated to 87° C. The remaining mercaptan was then added in two portions at 30 minute intervals, and within 3 hours of the beginning of the process, a single clear solution was obtained.

This solution was cooled, extracted with two portions of benzene, the benzene was discarded, and the solution was then acidified with dilute sulfuric acid. Two phases formed, and these were separated. The aqueous phase was extracted with benzene, which was added to the organic phase. The organic phase became milky and was cleared by addition of diethyl ether. Next, the solution was drained over sodium sulfate and stripped on a rotary evaporator to provide 22.2 grams of 3-butylthiopropionic acid product, and the yield was thus 68.5% of theoretical. The acrylic acid had a purity estimated at 97%, indicating that the 0.2 mole of sodium hydroxide was more than adequate to convert all of the acrylic acid actually used to sodium acrylate and leave about 0.006 mole of sodium hydroxide to act as the addition reaction base catalyst in accordance with the present invention.

COMPARATIVE EXAMPLE A

The pentaerythritol tetraester of 3-dodecylthiopropionic acid was prepared by transesterification of pentaerythritol with methyl 3-dodecylthiopropionate in accordance with the transesterification process of Dexter et al U.S. Pat. No. 3,758,549.

First, methyl 3-dodecylthiopropionate was prepared by adding dropwise with stirring 90.5 grams (1.05 mole) of methyl acrylate to 202.4 grams (1.0 mole) of lauryl mercaptan containing 0.5 gram of sodium methoxide. After 15 minutes, half of the methyl acrylate had been added, and the pot temperature was 75° C. The addition was complete in 30 minutes, and the pot temperature was 80° C. The reaction was allowed to stand for 1 hour and was shown by GLC. to contain 1.2% of several compounds from the lauryl mercaptan. The mixture was washed with 250 ml. of 5% aqueous hydrochloric acid and twice washed with water. The product was then stripped on a rotary evaporator to remove water and excess methyl acrylate. After filtration, the yield was 281.7 grams of colorless methyl 3-dodecylthiopropionate, which by GLC contained 98.1% product, 0.7% of an isomer, and 1.3% of lauryl mercaptan impurities.

A mixture of 144.1 grams (0.50 mole) of methyl 3-dodecylthiopropionate, 13.62 grams (0.10 mole) of pentaerythritol, and catalyst as shown below was heated with various means to remove methanol byproduct. A toluene-methanol azeotrope, vacuum, and nitrogen purge were used to remove methanol.

| Method of Removing Methanol | Scale | Sodium Methoxide Catalyst | Product Composition Tetra:Tris |
|---|---|---|---|
| Toluene azeotrope (no column) | 0.50 mole ester 0.10 mole PE | 0.50 g @ 0 time 0.50 g @ 6.5 hr 0.50 g @ 13.5 hr | 9 hr 49:51 12 hr 63:37 20 hr 84:16 |
| Aspirator (11 mm) | 0.25 mole ester 0.05 mole PE | 0.50 g @ 0 time 0.50 g @ 22 hr | 2 hr 58:42 6 hr 57:43 |
| | | | 22 hr 73:27 |
| | | | 26 hr 72:28 |
| | | | 29 hr 79:21 |
| Vacuum (18 mm) | 0.25 mole ester 0.05 mole PE | 0.50 g @ 0 time 0.50 g @ 2 hr 0.50 g @ 4 hr 0.50 g @ 6 hr 0.50 g @ 24 hr | 6 hr 69:31 24 hr 74:26 29 hr 75:25 |
| N₂ stream ⅛" into mixture | 0.25 mole ester 0.05 mole PE | 0.50 g @ 0 time 0.50 g @ 4 hr 0.50 g @ 25 hr | 6 hr 51:49 24 hr 77:23 29 hr 91:9 |
| N₂ stream to bottom of mixture | 0.25 mole ester 0.05 mole PE | 1.0 g @ 0 time | 4 hr 40:60 20 hr 82:18 28 hr 86:14 |
| Toluene azeotrope ten-plate Oldershaw column | 0.25 mole ester 0.05 mole PE | 0.25 g @ 0 time 0.25 g @ 25 hr | 6 hr 52:48 24 hr 74:26 30 hr 83:17 |
| Toluene azeotrope ten-plate Oldershaw column | 0.25 mole ester 0.05 mole PE | 0.25 g @ 0 time 1.22 g @ (0.01 mole) of 4-DMAP as co-catalyst | 4 hr 50:50 6 hr 63:37 |
| Toluene azeotrope ten-plate Oldershaw column | 0.25 mole ester 0.05 mole PE | 0.25 g @ 0 time | 2 hr 42:58 4 hr 46:54 6 hr 58:42 8 hr 62:38 24 hr 80:20 |
| Vacuum (17 mm) | 0.40 mole ester 0.05 mole of PE | 0.50 g @ 0 time | 6 hr 58:42 8 hr 58:42 24 hr 65:35 |
| Vacuum (17 mm) | 0.40 mole ester 0.05 mole PE | 0.50 g @ 0 time 0.50 g @ 6 hr | 2 hr 41:59 4 hr 40:60 6 hr 37:63 8 hr 77:23 24 hr 81:19 |
| Toluene azeotrope ten-plate Oldershaw column | 0.25 mole ester 0.05 mole PE | 0.50 g of LiOCH₃ @ 0 time | 2 hr 93.2:6.8 4 hr 96.2:3.8 6 hr 94.5:5.5 |

None of the reactions using sodium methoxide as catalyst was satisfactory, requiring long reaction times and often repeated additions of catalyst. In the reactions using the toluene-methanol azeotrope and a ten-plate Oldershaw column (to improve efficiency), the odor of methyl acrylate was evident. This would indicate a reversal of the reaction is occurring. Also, the repeated addition of catalyst needed would indicate catalyst is being consumed by the reverse reaction. Although lithium amide (LiNH₂) was an excellent transesterification catalyst, after four hours the reaction had become yellow and the odor of methyl acrylate was noticeable, so that the result was unsatisfactory.

COMPARATIVE EXAMPLE B

Acid catalyzed and metal salt catalyzed transesterifications were also tried. Substantially the same conditions were used as in the reactions of Comparative Example A, with the following unsatisfactory results:

| Method of Removing Methanol | Scale | Catalyst | Product Composition Methyl Ester: Tris:Tetra |
|---|---|---|---|
| Toluene azeotrope ten-plate Oldershaw | 0.25 mole ester 0.05 mole PE | 0.5 ml methanesulfonic acid | 6.5 hr (no reaction) |

-continued

| Method of Removing Methanol | Scale | Catalyst | Product Composition Methyl Ester: Tris:Tetra |
|---|---|---|---|
| column Vacuum (18 mm) | 0.25 mole ester 0.05 mole PE | 1.00 g Fascat 4101 organotin catalyst | 5 hr 68:15:17 23 hr 20:9:71 |

COMPARATIVE EXAMPLE C

The procedure essentially as described in Kauder et al U.S. Pat. No. 4,080,364 was followed for preparation of a 3-octylthiopropionate pentaerythritol tetraester by the addition reaction of 1-octene with the pentaerythritol tetraester of 3-mercaptopropionic acid. 100.0 grams (0.205 mole) of the pentaerythritol tetraester of 3-mercaptopropionic acid were placed into a round bottom flask. An azo initiator (0.25 gram of Vazo-64) was dissolved in 105.8 grams (0.943 mole) of 1-octene. This mixture was then poured into a funnel. The contents of the flask were heated to 85°-90° C., and an additional 0.25 gram of Vazo-64 was added. The contents of the funnel were added slowly so as to maintain the temperature at about 100°-110° C. After addition was complete, the reaction composition was stirred at 90° C. for one hour, and at this time an additional 15 grams of 1-octene were added, and the mixture was stirred for an additional hour. Then, 20 ml. of water were added, and the free 1-octene was steam distilled out at 115° C. for 30 minutes. After cooling, filtering and washing with water, the organic material was extracted and stripped in a rotary evaporator. Analysis of the reactant product showed a product peak indicating pentaerythritol tetraester of 3-octylthiopropionic acid at 5.32 minutes amounting to 85.9%, but with a shoulder indicating an incompletely resolved impurity, along with 14% of a well resolved impurity, presumably a triester. The acid value of the product was 0.094.

COMPARATIVE EXAMPLE D

The process as specified in Synthetic Example 7 of Nakahara et al U.S. Pat. No. 4,349,468 was followed. 168.3 grams (1.0 mole) of 1-dodecene were combined with 0.5 gram of Vazo-64 (an azo compound catalyst), and 120.2 grams (1.13 mole) of 3-mercapto propionic acid were added dropwise. An exotherm occurred, the temperature reaching 85° C. The reaction composition was stirred for an additional three hours at 80° C., poured into water, and the solid precipitate was collected by filtration. Recrystallization from acetone yielded 240.2 grams of product. The recrystallized crude product gave an assay of 98.8% and a melting point of 60.5°-62° C. The crude product collected after filtration analyzed by GLC. as 95.6% product (3-dodecylthiopropionic acid), 4.4% isomer, and 1.3% unknown.

Esterification of product made according to this process in order to form the pentaerythritol tetraester of 3-dodecylthiopropionic acid results in a soft, waxy tetraester product found to be inferior to other tetraester products, such as when formed by way of the synthetic sequence starting with methyl acrylate, as specified in Comparative Example A hereinabove.

It will be understood that the embodiments of the present invention which have been described are illustrative of some of the applications of the principles of the present invention. Numerous modifications may be made by those skilled in the art without departing from the true spirit and scope of the invention.

We claim:

1. A process for preparing a 3-alkylthiopropionic acid wherein the alkyl group thereof has between about 4 and about 20 carbon atoms, comprising:
   (a) providing an alkyl mercaptan of the formula RSH, wherein R is an alkyl group having from about 4 to about 20 carbon atoms;
   (b) reacting said alkyl mercaptan by a direct addition reaction with a charge of an acrylic component selected from the group consisting of acrylic acid or an alkali metal acrylate and blends thereof, said reacting step being carried out in an alkaline reaction solution and in the presence of an aqueous alkaline catalyst that is a strong base which is present in the reaction solution at a molar concentration in excess of that of any acrylic acid in the reaction solution, wherein said reaction solution is at a pH of at least about 11; and
   (c) acidifying the reaction solution and recovering a water-insoluble phase as 3-alkylthiopropionic acid.

2. The process according to claim 1, wherein said reaction solution is an aqueous alkaline solution including a solvent mixture of water and an organic solvent.

3. The process according to claim 2, wherein said organic solvent is a water soluble oxygenated compound.

4. The process according to claim 1, wherein said acidifying step is carried at a pH of about 4 or below.

5. The process according to claim 1, wherein said alkyl mercaptan and said acrylic component are at substantially equimolar concentrations.

6. The process according to claim 1, wherein said alkaline catalyst is a strong base, and wherein a 1% aqueous solution thereof has a pH of at least about 13.

7. The process according to claim 1, wherein said alkaline catalyst is an alkali metal hydroxide.

8. The process according to claim 1, wherein at least about 1.05 mole of the alkaline catalyst is added per mole of charged acrylic acid.

9. A process for preparing a pentaerythritol tetraester of a 3-alkylthiopropionic acid wherein the alkyl group thereof has between about 4 and about 20 carbon atoms, comprising:
   (a) providing an alkyl mercaptan of the formula RSH, wherein R is an alkyl group having from about 4 to about 20 carbon atoms;
   (b) reacting said alkyl mercaptan by a direct addition reaction with acrylic acid or an alkali metal acrylate, said reacting step being carried out in an alkaline reaction solution and in the presence of an aqueous alkaline catalyst that is a strong base which is present in the reaction solution at a molar concentration in excess of that of any acrylic acid in the reaction solution, wherein said reaction solution is at a pH of at least about 11;
   (c) acidifying the reaction solution and recovering a water-insoluble phase as -b 3-alkylthiopropionic acid;
   (d) reacting said 3-alkylthiopropionic acid with pentaerythritol in order to form a pentaerythritol tetraester of 3-alkylthiopropionic acid product; and
   (e) solvent refining said pentaerythritol tetraester 3-alkylthiopropionic acid product with a blend of organic solvents selected from the group consisting of a blend of lower aliphatic alcohols and a blend of a lower aliphatic alcohol with a lower aliphatic ester of a lower aliphatic carboxylic acid.

10. The process according to claim 9, wherein said blend of organic solvents is a blend of a lower aliphatic alcohol with a lower aliphatic ester of a lower aliphatic carboxylic acid.

11. The process according to claim 9, wherein said R group of the mercaptan has a carbon chain length of about 12, and wherein said organic solvent blend is a combination of isopropanol and isopropyl acetate.

12. The process according to claim 9, wherein said R group of the mercaptan has a carbon chain length of about 8, and wherein said organic solvent blend is a combination of methanol and isopropanol.

13. The process according to claim 9, wherein said alkyl mercaptan and said acrylic component are at substantially equimolar concentrations, and said alkaline catalyst is an alkali metal hydroxide added at a concentration of at least about 1.05 mole per mole of charged acrylic acid.

* * * * *

UNITED STATES PATENT AND TRADEMARK OFFICE
CERTIFICATE OF CORRECTION

PATENT NO. : 5,057,622

DATED : October 15, 1991

INVENTOR(S) : Chisholm et al.

It is certified that error appears in the above-identified patent and that said Letters Patent is hereby corrected as shown below:

Col. 6, line 39, "C. With stirring." should read --C. with stirring.--
Col. 9, line 44, "GLC." should read --GLC--.
Col. 11, line 56, "GLC." should read --GLC--.
Col. 12, line 61, delete "-b".

Signed and Sealed this

Twelfth Day of October, 1993

Attest:

BRUCE LEHMAN

Attesting Officer

Commissioner of Patents and Trademarks